United States Patent [19]

Pang et al.

[11] Patent Number: 5,192,664
[45] Date of Patent: Mar. 9, 1993

[54] PARATHYROID HYPERTENSIVE FACTOR, ANTIBODIES AND USES THEREOF

[75] Inventors: Peter K. T. Pang, 52225 Range Road 232, 205 Carriage Lane, Sherwood Park, Alberta, Canada, T8A 245; Richard Z. Lewanczuk, Edmonton, Canada; Christine G. Benishin, Ardossen, Canada; Toyoii Kaneko, Kanagawa, Japan

[73] Assignee: Peter K. T. Pang, Alberta, Canada

[21] Appl. No.: 603,745

[22] PCT Filed: Nov. 21, 1990

[86] PCT No.: PCT/US90/01577
§ 371 Date: Nov. 21, 1990
§ 102(e) Date: Nov. 21, 1990

[87] PCT Pub. No.: WO90/11074
PCT Pub. Date: Oct. 4, 1990

Related U.S. Application Data

[63] Continuation-in-part of Ser. No. 327,450, Mar. 22, 1989, abandoned, and a continuation-in-part of Ser. No. 460,482, Jan. 3, 1990.

[51] Int. Cl.$^5$ .................... C12Q 1/00; C07K 15/00
[52] U.S. Cl. .................... 435/79; 435/7.92; 435/70.21; 435/240.26; 424/85.8; 436/518; 436/548; 530/806; 530/800; 530/300
[58] Field of Search .............. 436/539, 518, 541, 548, 436/808, 811; 435/7.9, 7.92, 70.1, 70.21, 240.26, 240.27, 975; 530/412, 414, 417, 806, 800, 350, 395, 300; 424/9, 85.8

[56] References Cited

U.S. PATENT DOCUMENTS 4,250,084  2/1981  Trainin et al. ............... 260/112 R

OTHER PUBLICATIONS

Wright et al. "The Vascular Seweitizing Character of Plasma from Spontaneously Hypersensitive Roots" Cand. J. Physiol. Pharmacol. 59:1111–1116 1981.
Yoshimi et al. "A Novel Human Plasma Factor Capable of Mobilizing Intracellular $Ca^{+2}$ in Cultured Rat Vascular Smooth Muscle Cells" Biochem. & Biophys. Rsch Comm. vol. 153, No. 3, 1988 pp. 1068–1075.
Maurea et al. Methods in Enzymology, vol. 70 p. 49–70 Academic Press, N.Y. N.Y. 1980.
Lehringer et al. Biochemistry pp. 157–161, Worth Pub. N.Y. N.Y. 1970.
Roitsch et al. Immunological Methods vol. III, pp. 86–87 Academic Press, N.Y. N.Y. 1985.
Prave et al Fundamentals of Biotechnology pp. 280–289 & 482–491 VCH Pub. Weinheim, Germany 1987.

Primary Examiner—Sam Rosen
Attorney, Agent, or Firm—Nikaido, Marmelstein, Murray & Oram

[57] ABSTRACT

A new circulating factor from the parathyroid gland of some hypertensive mammals have been isolated and characterized. Polyclonal and monoclonal antibodies raised against this factor are usable as a screen for the presence of the factor. The factor is involved in the control of calcium uptake in cells. Hypertensive mammals may be treated to lower mean blood pressure by administering a calcium channel blocking agent together with one or both of a calcium supplement and Vitamin D. The hypotensive effect of this combination is synergistic and the dose response is more predictable than the administration of any of these agents singly. The factor has a molecular weight of 3,000 to 4,000 Daltons.

15 Claims, 17 Drawing Sheets

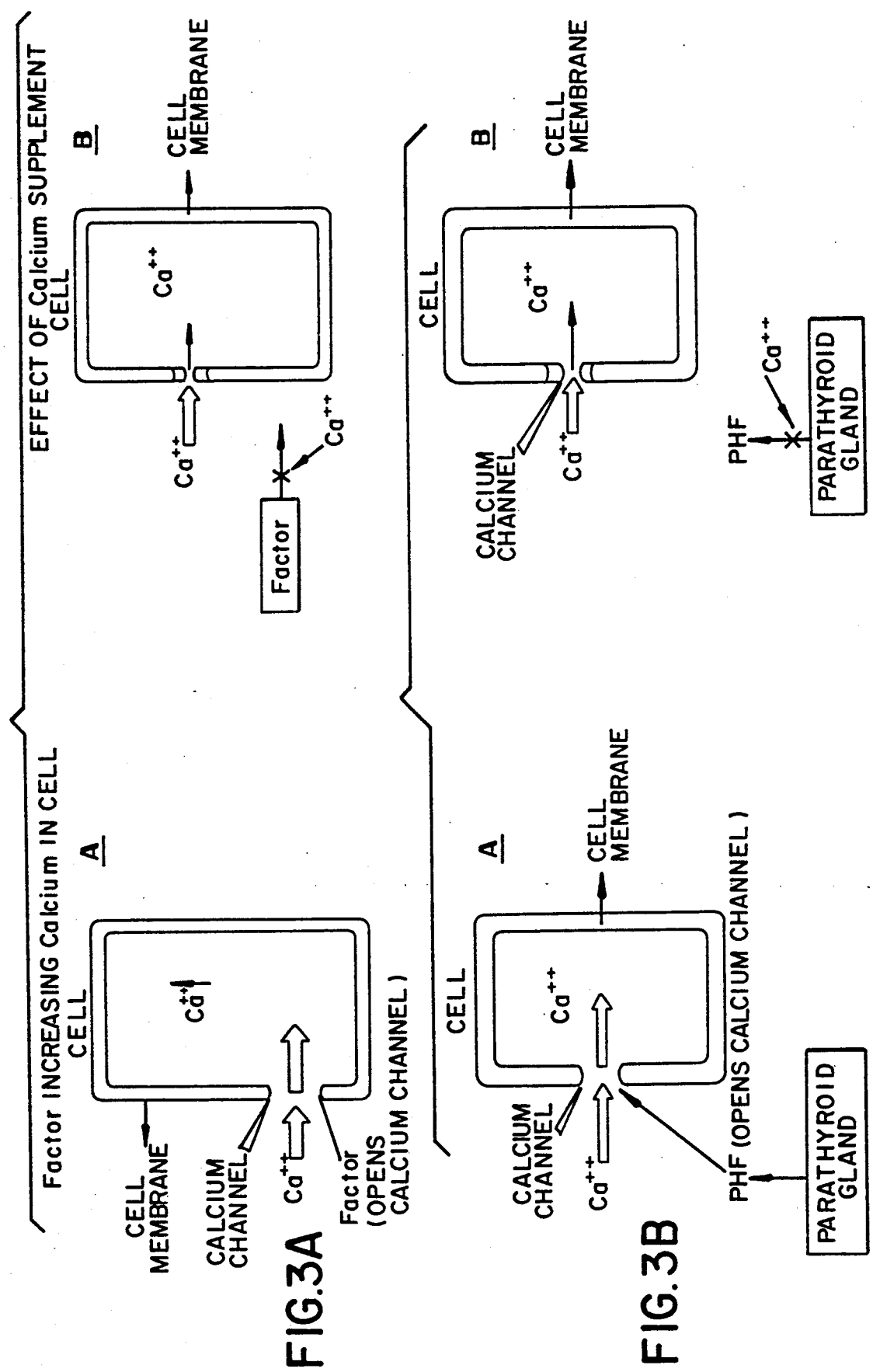

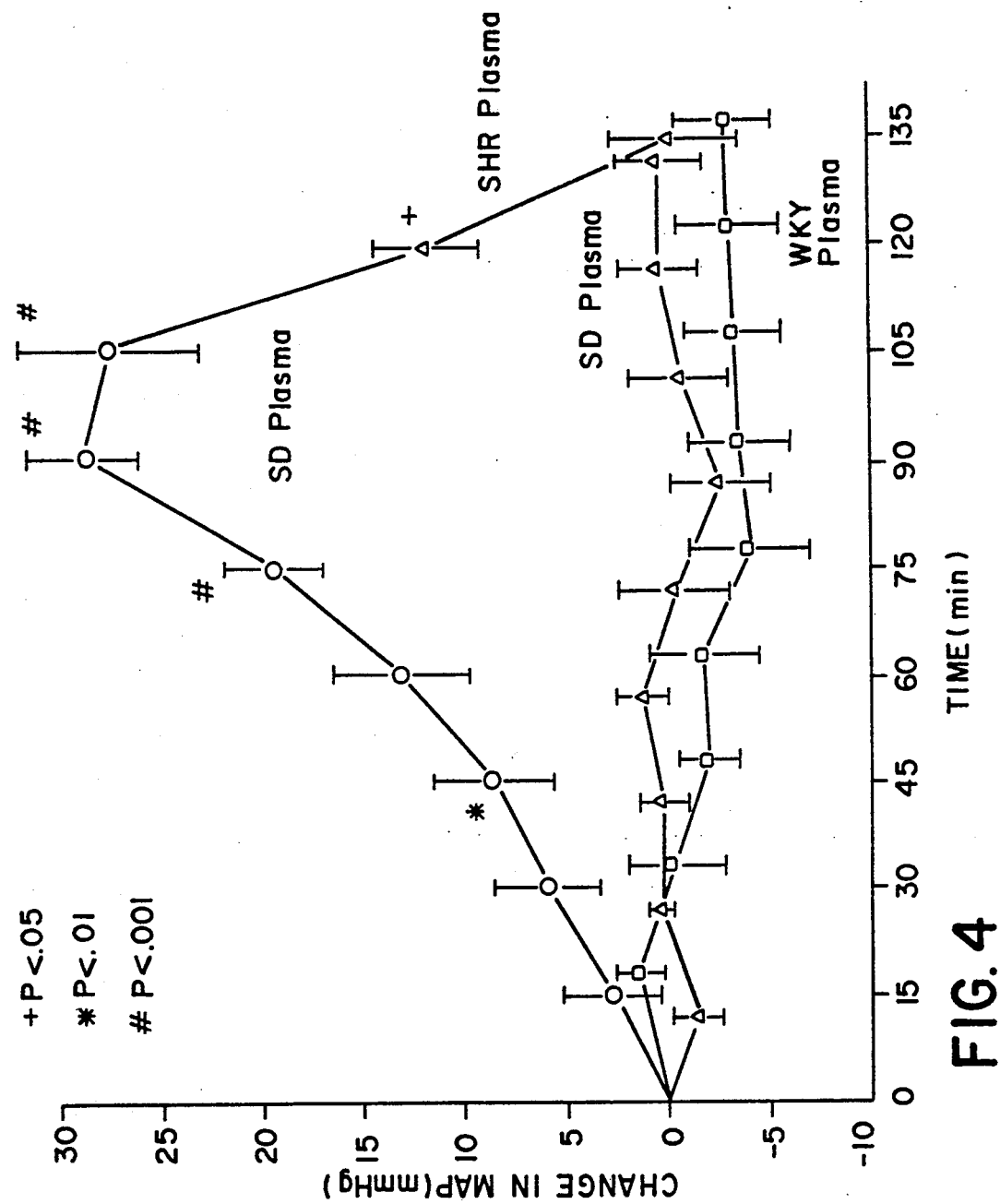

STANDARD
14 KD

SD
PTH GLAND EXTRACT

SHR
PTH GLAND EXTRACT

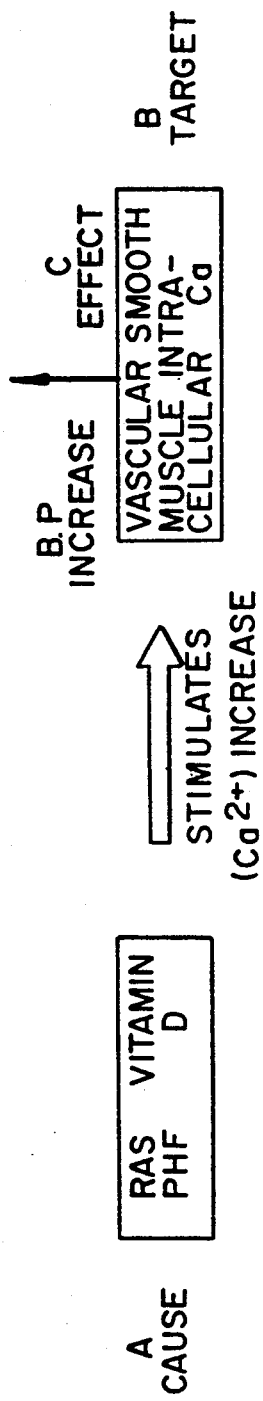
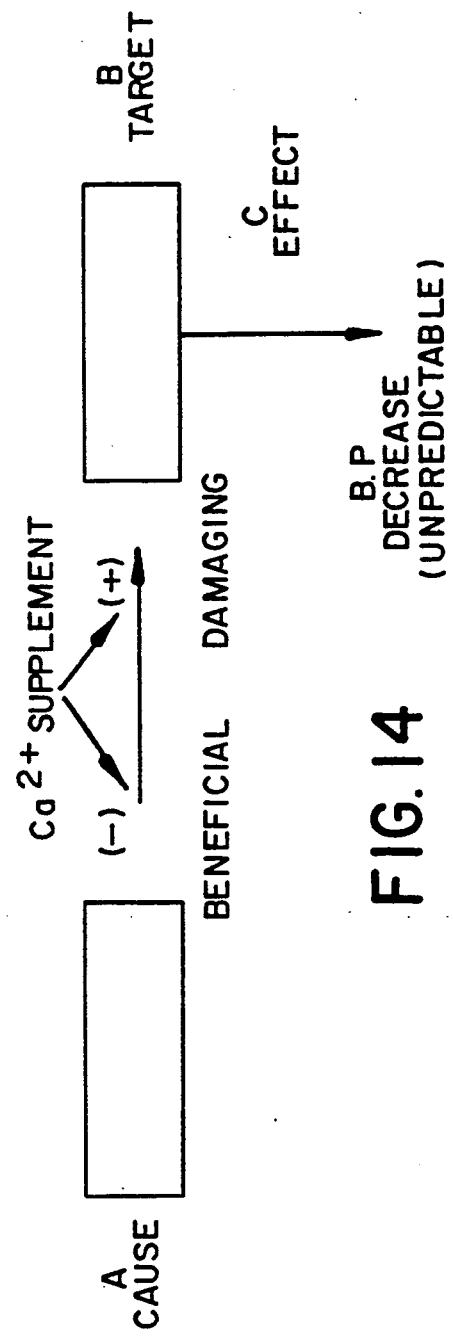
FIG. 13
FIG. 14

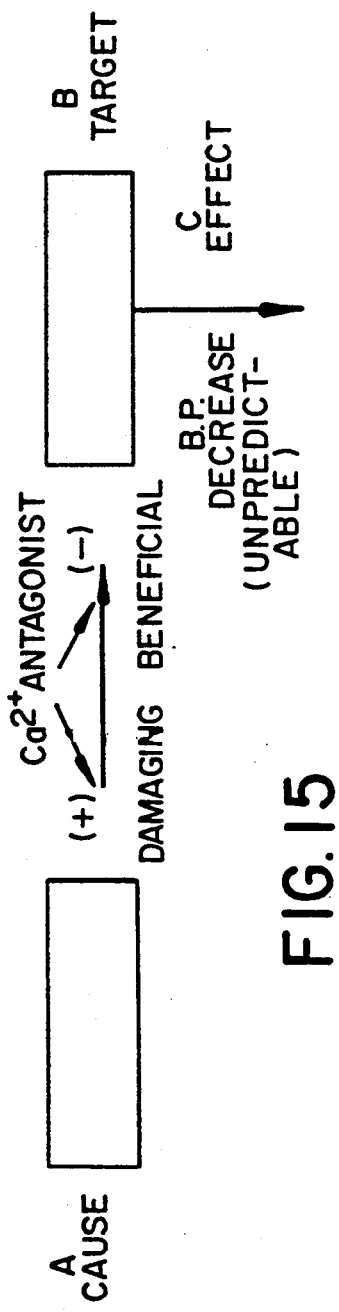
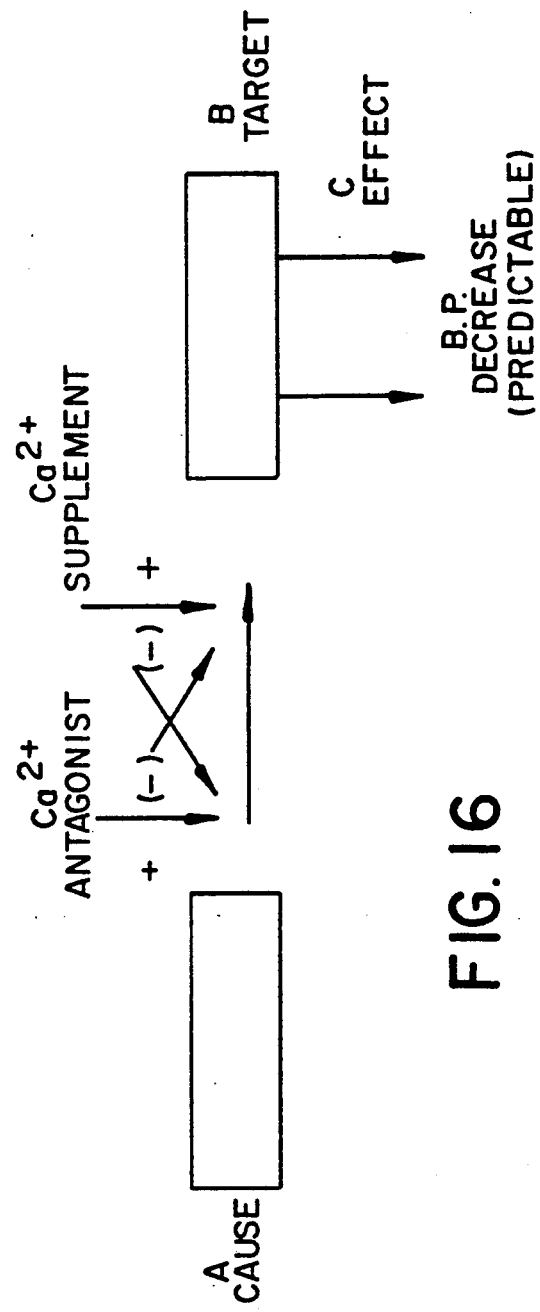

a - α-CHYMOTRYPSIN - 8.8
b - WHALE MYOGLOBIN - 8.05
c - EQUINE MYOGLOBIN - 7.0
d - HUMAN CARBONIC ANHYDRASE - 6.5
e - BOVINE CARBONIC ANHYDRASE - 6.0
f - β-LACTOGLOBULIN - 5.1
g - PHYCOCYANIN - 4.65

PARATHYROID HYPERTENSIVE FACTOR, ANTIBODIES AND USES THEREOF

This application is a continuation-in-part of U.S. patent application Ser. No. 327,450, filed Mar. 22, 1989, now abandoned and a continuation-in-part of U.S. patent application Ser. No. 460,482, filed Jan. 3, 1990.

FIELD OF THE INVENTION

This invention relates to a previously unidentified circulating factor having its origin in the parathyroid gland. This factor is related to control of cellular calcium uptake, and is particularly related to hypertension and some other diseases in mammals. The circulating factor has been isolated, and methods for screening patients for the presence of the circulating factor are described. The factor is useful in the assessment of patients with diseases which involve intracellular calcium elevation and in the study of other diseases in which calcium is involved. The presence of this factor in patients indicates novel therapeutic treatments.

BACKGROUND OF THE INVENTION

Hypertension is generally defined as the elevation of the systolic and/or diastolic arterial blood pressure above a nominal value of 140/90 mm Hg. Diseases associated with hypertension include arteriosclerosis, hypertensive renal failure, stroke, congestive heart failure and myocardial infarction. Although numerous methods of treatment have been found to be effective in the reduction of arterial blood pressure, the etiology of essential hypertension remains essentially unknown. A genetic predisposition to hypertension is generally accepted, but the number of different drugs which have been found effective in the treatment of hypertension, and the fact that these drugs seem to operate by eliciting different pharmacological responses, suggests that there may be different primary causes for essential hypertension.

A number of studies have suggested that one or more circulating factors may play a role in the genesis or the maintenance of hypertension [See: Wright et al., A Hypertensive Substance Found in the Blood of Spontaneously Hypertensive Rats; *Life Sci.* 1984; 34:1521-1528; Dahl et al., Humoral Transmission of Hypertension: Evidence from Parabiosis; *Circ. Res.* 1969; 24/25 (Suppl. I):21-23; Greenberg et al., Evidence for Circulating Factors as a Cause of Venous Hypertrophy in Spontaneously Hypertensive Rats; *Am. J. Physiol.* 1981; 241:H421-H430; Tobian et al., A Circulating Humoral Pressor Agent in Dahl S Rats with Salt Hypertension; *Clin. Sci.* 1979; 57:345s-347s; Zidek et al., Humoral Factors in the Pathogenesis of Primary Hypertension; *Klin. Wochenschr.* 1985; 63 (Suppl. II) D:94-96; Hirata et al., Hypertension Producing Factor in the Serum of Hypertensive Dahl Salt-Sensitive Rats; *Hypertension* 1984; 6:709-716]. For example, in parabiosis and cross-circulation experiments, an increase in blood pressure could be induced in normotensive animals by exposure to blood from hypertensive animals. The subcutaneous injection of erythrocyte-associated factor obtained from spontaneously hypersensitive rats (SHR) has been shown to induce hypertension in normotensive Wistar-Kyoto (WKY) rats and an increase in blood pressure can be induced in normotensive, salt sensitive Dahl rats by injection of serum from hypertensive, salt-sensitive Dahl rats.

There have also been reports of circulating factors in both hypertensive rats and hypertensive humans which increase intracellular calcium [See: Banos et al., Two Factors Associated with Increased Uptake of Calcium in Platelets from Essential Hypertensive Patients; *Clin. Exp. Hypertens.* 1987; 9:1515-1530; Zidek et al., Effect of Plasma from Hypertensive Subjects on Ca Transport in Permeabilized Human Neutrophils; *Clin. Sci.* 1988; 74:53-56; Linder et al., Effects of a Circulating Factor in Patients with Essential Hypertension on Intracellular Free Calcium in Normal Platelets; *N. Enc. J. Med. 1987; 316:509-513;* Bruschi et al., Cytoplasmic Free Ca is Increased in the Platelets of Spontaneously Hypertensive Rats and Essential Hypertensive Patients; *Clin. Sci.* 1985; 68:179-184; Wright et al., Stimulation of Aortic Tissue Calcium Uptake by an Extract of Spontaneously Hypertensive Rat Erythrocytes Possessing Hypertensive Properties; *Can. J. Physiol. Pharmacol.* 1986; 64:1515-1520]. Since vascular tone is influenced by the level of intracellular calcium, it would seem reasonable to assume—although it has not yet been experimentally shown—that factors which increase blood pressure and factors which increase intracellular calcium may be related. There has been accumulating evidence suggesting the involvement of calcium regulating hormones in some forms of hypertension [See: L. M. Resnick, *Am. J. Med.* 82 (Suppl. 1B), 16 (1987)]. Parathyroid hormone (PTH) is a calcium regulating hormone. Thirty percent or more of essential hypertensive patients fall into a subgroup characterized by increased levels of immunoreactive parathyroid hormone (ir-PTH). [See: Laragh et al., *Kidney Int.* 34, (Suppl. 35), S162 (1988)]. An increase in PTH levels has been reported in SHR rats [See: McCarron et al., *Hypertension* 3 (Suppl. 1), I162 (1981)] and it has been observed that hyperparathyroid patients often exhibit hypertension, the severity of which can, in most cases, be reduced by parathyroidectomy [See: Hellstrom et al., *Brit. J. Urol.* 30, 13 (1958)]. Similar results from parathyroidectomy have also been reported in SHR rats. [See: Schleiffer et al., *Jap. Circ. J.* 45, 1272 (1981)]. Various investigators have suggested that PTH contributes to the development of essential hypertension, although exogenous administration of PTH causes a reduction in blood pressure in mammals and other vertebrates [See: Pang et al., *Gen. Comp. Endocrinol.* 41, 135 (1980)]. This vasodilating action of PTH also has been related to a specific region of the molecule separate from the region mediating hypercalcemic effects [See: Pang et al., *Endocrinology*, 112, 284 (1983)]. pTH has also been shown to inhibit calcium entry into vascular smooth muscle [See: Pang et al., *Lifr Sci.,* 42, 1395 (1988)] through L-type calcium channels [Wang et al., submitted for publication]. This paradox is further heightened by the fact that hypertensive patients with increased PTH levels exhibit decreased serum ionized calcium levels [See: Resnick et al., *New Encl. J. Med.,* 309, 888 (1983); Hvarfner et al., *Acta Med. Scand.,* 219, 461 (1986)]. It would be expected that the serum ionized calcium levels would be elevated if PTH were primarily elevated.

The involvement of the parathyroid gland in essential hypertension has been apparent but existing literature on the action of PTH on the vasculature is not consistent with a causative role for PTH in essential hypertension. At the time that this invention was made, PTH was the only active hormone reported to be produced by the parathyroid gland.

Calcium channel blockers were identified as a method for the control of hypertension, as reported by Fleckenstein et al., Z. Kreislaufforsch, 56, 716 (1967), and are routinely used in the control of hypertension. Three calcium channel blockers are currently of clinical significance in the United States, verapamil, nifedipine and diltiazem. All three achieve their anti-hypertensive effect by inhibiting the entry of calcium ions into vascular smooth muscle. The ultimate effect is vasodilation calcium channel blockers, by limiting the uptake of calcium-in vascular smooth muscle, are beneficial, but have been found to stimulate some endocrine systems, such as the RAS system. [Kotchen et al., Am. J. Cardiol., 62 41G (1988); Matsumara et al., J. Pharmacol. Exp. Ther., 241, 1000 (1978); Resnick et al., Fed. Proc., 45, 2739 (1986)]. Utilization of calcium -channel blockers may be limited by excessive vasodilation, negative inotropy, excessive depression of the sinus nodal rate, atrial-ventricular nodal conduction disturbances and interference with non-vascular smooth muscle contraction. A combination therapy which minimizes the amount of calcium channel blocker required to achieve the desired anti-hypertensive effect is desirable.

BRIEF SUMMARY OF THE INVENTION

The presence of a previously unreported circulating factor, having its origin in the parathyroid gland, now has been demonstrated in SHR rats and in many humans having essential hypertension. The factor has been shown to regulate cellular calcium uptake, and can be inhibited by increases in dietary calcium levels. The factor has been isolated and a method for screening for the factor using antibodies raised against the factor is described. The factor has a molecular weight of approximately 3000-4000. From bioassay data, the factor in humans and rats has been found to be substantially similar.

The circulating factor appears to be present in a substantial proportion—but not all—of the human population having essential hypertension and is particularly associated with low-renin hypertension. Identification of the circulating factor in hypertensive patients may be used to design and monitor therapy to counteract its effects.

It further has been discovered that the use of supplemental dietary calcium and calcium channel blockers in combination is an effective method of treatment for hypertension and that the combination therapy employing both agents is more effective and predictable than the use of either agent alone. The effect is greater than the sum of the effects of both agents separately, or synergistic. Alternatively, the administration of compounds which have an effective form of Vitamin D, such as $1\alpha,25$-dihydroxycholecalciferol ($1,25$-$(OH)_2D_3$), which increases intestinal calcium absorption, together with a calcium channel blocker, is a convenient treatment modality.

BRIEF DESCRIPTION OF THE DRAWINGS

FIG. 3 is a schematic representation of the mechanism of calcium entry into cells and control of the mechanism.

FIG. 4 shows the change in mean arterial pressure in SD rats infused with plasma obtained from SHR, SD and WKY rats.

FIG. 13 illustrates the method of stimulating vascular smooth muscle contraction by systems which increase calcium uptake.

FIG. 14 illustrates the beneficial and damaging effects of calcium supplementation alone.

FIG. 15 illustrates the beneficial and damaging effects of calcium antagonists.

FIG. 16 illustrates the advantages of combination therapy.

DETAILED DESCRIPTION OF THE INVENTION

Figure 1:
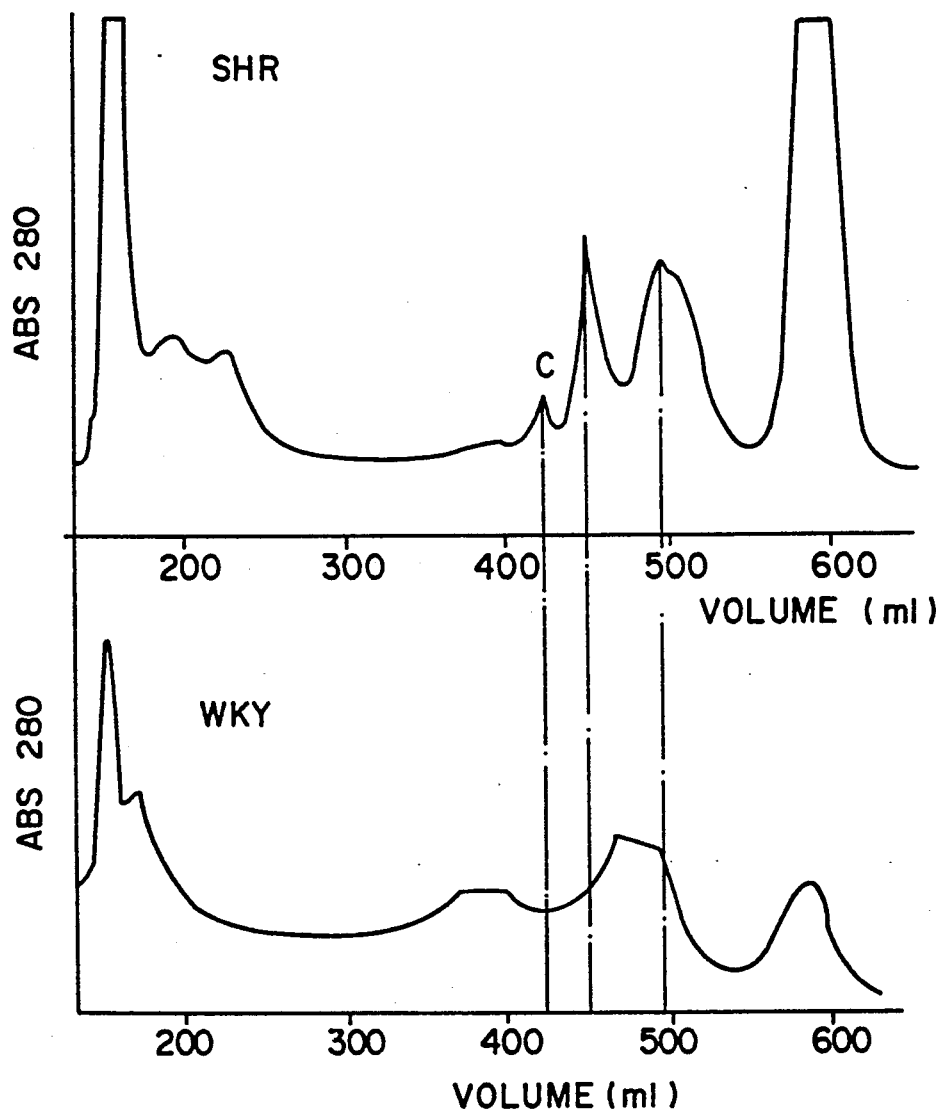
FIG. 1 is an elution profile for plasma for SHR rats according to Example 3.

The existence of a circulating factor in the blood of the SHR rat was confirmed by the studies which we reported in Am. J. Hypertens., 2, 26-31 (1989). In these studies, we showed an increase in the blood pressure of WKY and SD rats when plasma from SHR rats was injected into the normotensive rats either by infusion or by bolus injection. In addition, we have shown that the uptake of $^{45}Ca$ by sections of the tail artery of a rat, in vitro, increased in a dose-dependent manner as the concentration of SHR plasma was increased in a buffer-based medium. The results of these experiments clearly show that an increase in blood pressure and an increase in calcium uptake in the cells were both dose-dependent on the amount cf SHR plasma present and available in the system. Curiously, the onset of both events was delayed, and gradual, whereas known endogenous pressor agents such as norepinephrine, angiotensin II and vasopressin have been observed to increase blood pressure almost immediately and quite rapidly after administration. Another result observed in these studies was that when the infusion of SHR plasma was stopped and substituted with plasma from normotensive rats, the observed blood pressure decreased quite rapidly to the baseline. The decrease observed precluded a simple volume effect. In a related experiment, dialyzed plasma from normotensive and hypertensive human subjects was infused into normotensive SD rats and shown to produce hypertension. Plasma from these subjects also increased calcium uptake in rat tail arteries in vitro.

The origin of the circulating factor was unknown, but the anecdotal reports that PTH was elevated in hypertensive rats suggested the parathyroid gland as a target of investigation. Parathyroidectomies of SHR rats were found to reduce blood pressure and plasma from the SHR rats which had been parathyroidectomized did not cause elevation of blood pressure in normotensive rats. Conversely, transplantation of parathyroid glands from SHR rats to normotensive Sprague-Dawley (SD) rats resulted in an increase in blood pressure and the appearance of the factor in the plasma, as shown by infusion of the isolated plasma into other normotensive rats. Pang and Lewanczuk, *Amer. J. Hypertens.*, 2, 898 (1989).

On the basis of these studies, we concluded that the parathyroid was the origin of the circulating factor and have proposed the name "Parathyroid Hypertensive Factor" or PHF for this substance.

A potential complicating factor in the experiments described above could be the presence of calcium and other small molecular weight pressor substances in elevated concentration(s) in the transfused plasma. To eliminate this possibility, all plasma which was to be transfused was dialyzed overnight using a membrane having a molecular weight cut-off of approximately 1,000. This procedure should be effective in removing calcium, and also most known endogenous pressor agents including the ouabain-like factors, which are reported to have a molecular weight range of 400-500. Furthermore, all known endogenous pressor agents act rapidly.

To isolate and identify PHF from plasma, SHR rats, WKY rats and SD rats were decapitated, and exsanguinated, and the collected plasma of each type was centrifuged after being treated with heparin. The collected plasma was first dialyzed (molecular weight cut-off 1,000), filtered through an ultrafiltration system having an upper cut-off of approximately 5,000 m.w., and the collected filtrate concentrated by lyophilization. The concentrated dialysate was applied to a molecular sieve column such as Bio-Gel P-6. Upon elution with 0.05 M NH$_4$OAc at pH 7.0, the fractions were collected. Elution was monitored photometrically at 280 nm using a Pharmacia U.V. detector and a fraction was identified in the plasma from SHR rats which was absent in the samples obtained from normotensive rats (See FIG. 1).

The anomalous fractions from SHR rats were combined, concentrated by lyophilization and injected into normotensive rats. An increase in blood pressure was observed with the delayed onset (30-45 minutes) characteristic of plasma from SHR rats. Fractions of the same elution position from normotensive rat plasma preparations did not show such activity. The active component in the anomalous SHR fraction was estimated to have a molecular weight of approximately 3,500 daltons by molecular exclusion and chromatography using both liquid chromatography columns and HPLC.

Figure 2A:
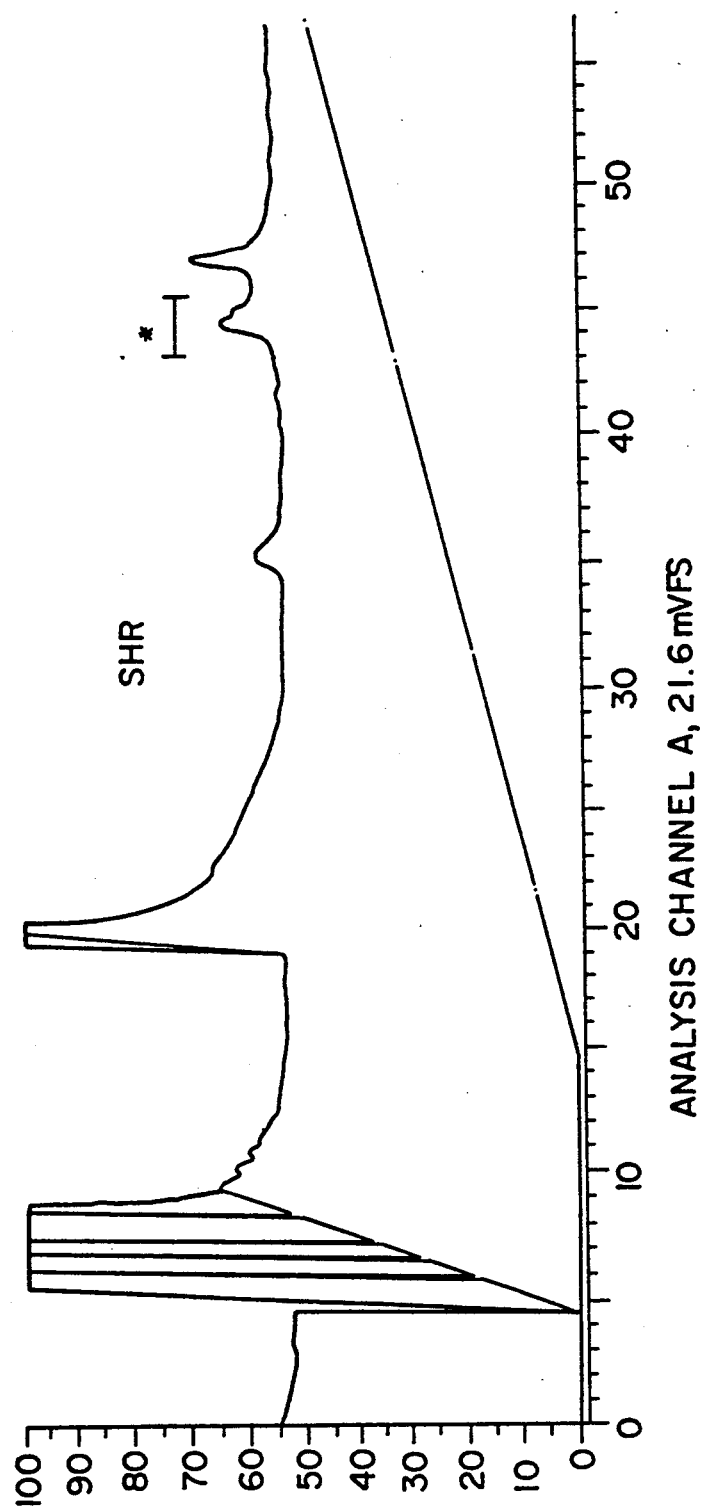
FIG. 2(a) is a reverse phase HPLC separation profile of the plasma sample of FIG. 1 from SHR rats.
Figure 2B:
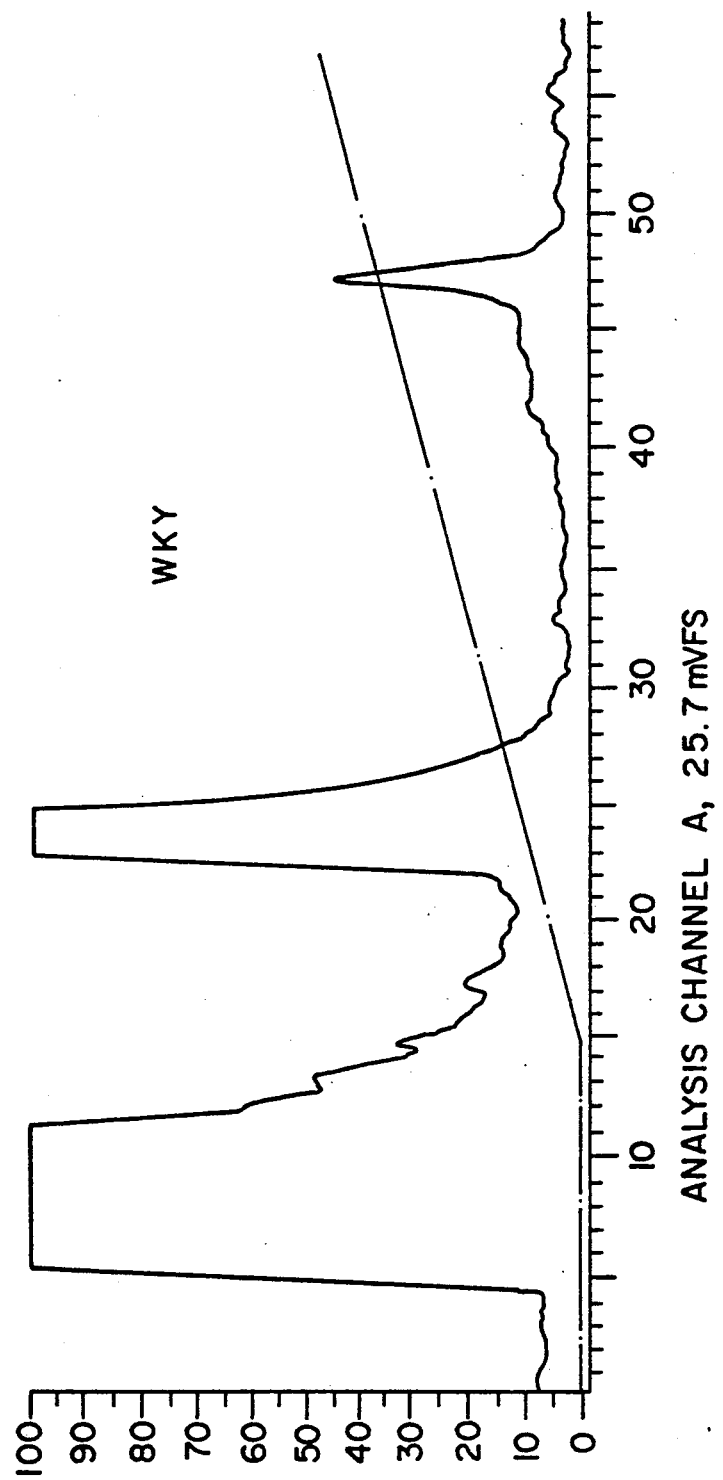
FIG. 2 (b) is an HPLC profile of the plasma from WKY rats.

To further characterize the active fraction, the plasma samples were lyophilized and fractionated on a Brownlee RP-P (C-8) reverse phase column HPLC using a gradient 0.1% trifluoroacetic acid: acetonitrile solvent, again monitoring the eluate at 280 nm. The results are shown in FIGS. 2(a) and 2(b).

Figure 8A:
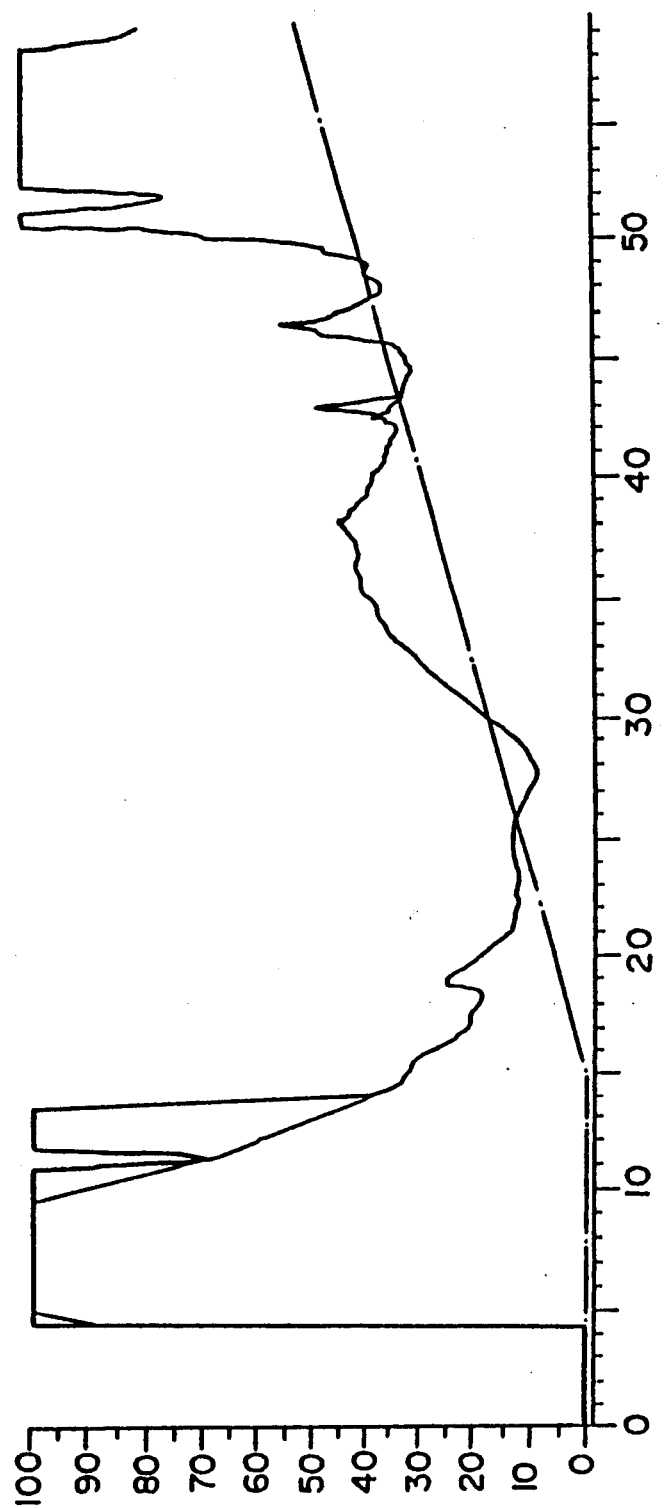
FIG. 8(a) is a reverse phase HPLC profile of culture media from a thyroparathyroid gland cell culture using thyroid glands from SHR rats.
Figure 8B:
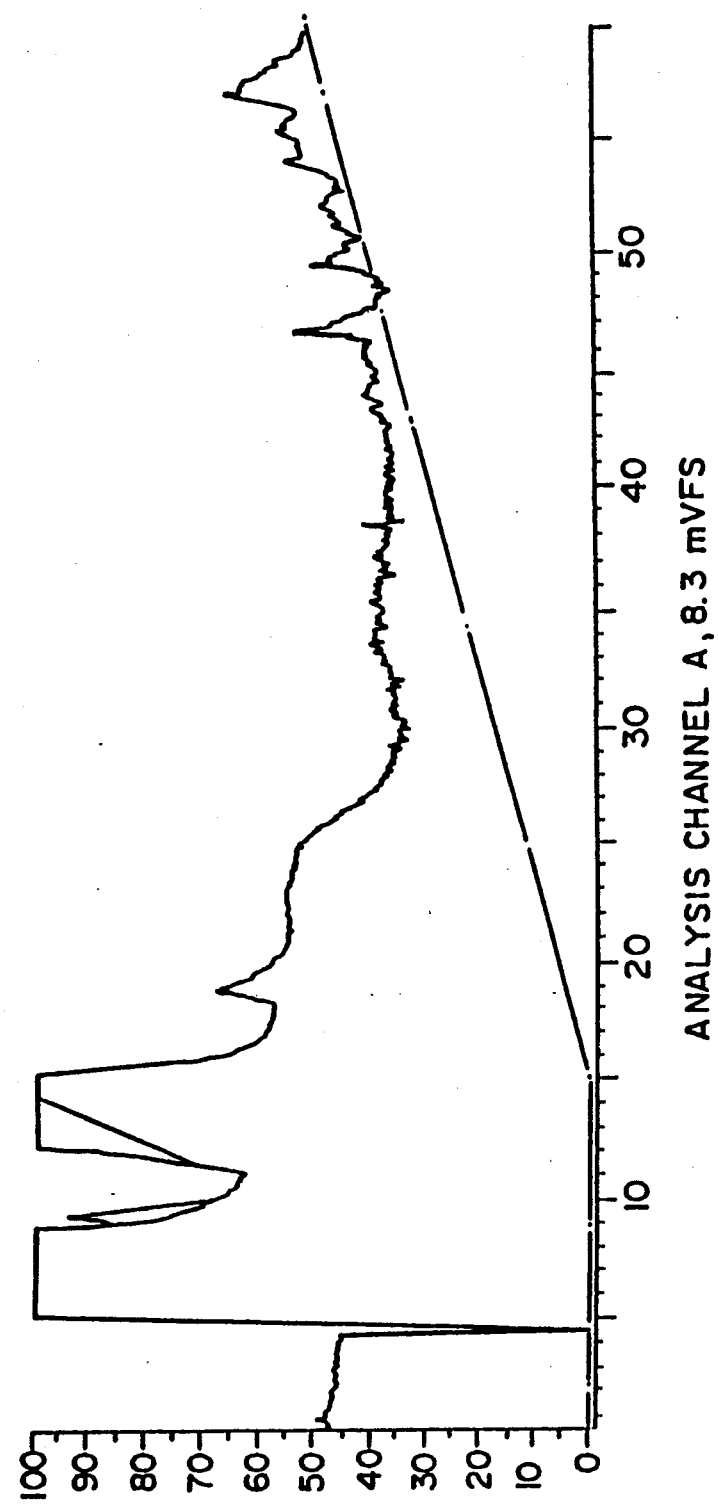
FIG. 8(b) is a comparative profile for thyroparathyroid cell culture media from WKY rats.

Thyroparathyroid glands were excised from SHR rats and cultured for up to 7 days in Hank's medium (Gibco), with the media changed daily. The production of PHF may be stimulated by reduction of calcium from the medium. Pooled media, after dialysis and filtration analogous to the treatment of plasma samples, was lyophilized and fractionated by HPLC using a reverse phase column. FIG. 8(a) illustrates the separation. FIG. 8(b) illustrates the result when glands from WKY rats were used.

Primary cell cultures prepared from SHR and SD rats were grown as described above. At 4 hour intervals, samples of the media were removed and lyophilized. After resuspension in a minimum mount of distilled H$_2$O, the extracts were spotted on an SDS-PACE gel (15-18% acrylamide/bisacrylamide) and developed for approximately 1 hour and developed (Bio-Rad Mini-Protein II). After staining with coomassie blue or, preferably, silver, the gels were scanned. The results are shown in FIG. 10. An unique peak appears in the medium from SHR rat cells which is not present in SD rat cell media or in SHR rat cell media prior to about 12 hours. The molecular weight for the peak is estimated at about 3,300 daltons.

In a related experiment, thyroparathyroid cells were cultured as described. After 8 hours, the cells were removed from culture, homogenized in 50 mM acetic acid, centrifuged at ca. 5,000$\times$g to remove cell debris and run on a 10-18% acrylamide/bisacrylamide gel. The results are shown in FIG. 9.

Figure 17:
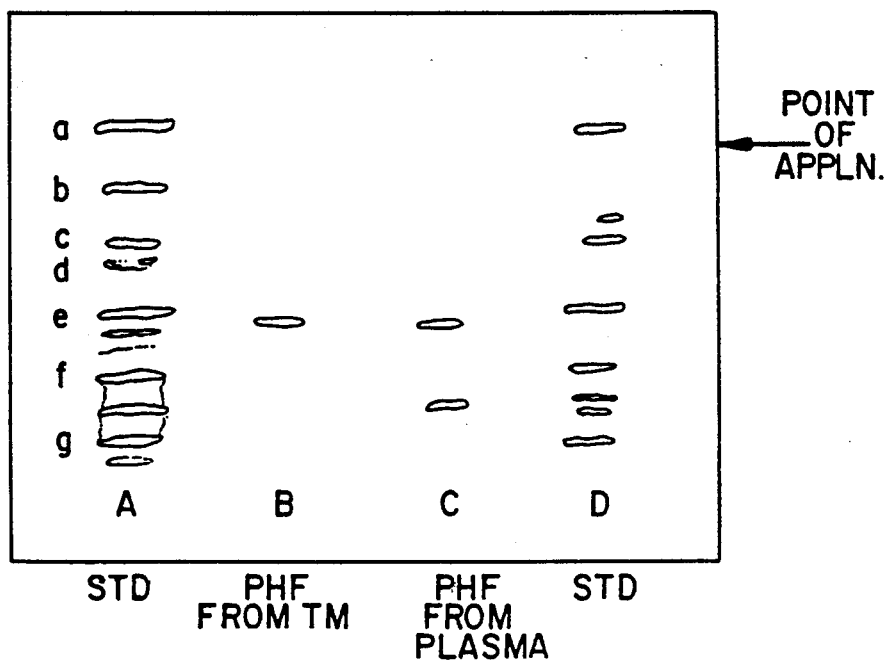
FIG. 17 is an isoelectric focusing gel of PHF plasma and cell culture media

The isoelectric point for PHF from SHR thyroparathyroid media or plasma was determined on two gels, IEF and SDS-PAGE using a Bio-Rad mini-isoelectric focusing system and a pH 3-10 ampholyte gradient. The results are shown in FIG. 17, indicating a common spot at about pH 6.

The total RNA from PHF-producing cells may be extracted using conventional techniques [c.f. Maniatis, T, et al. *Molecular Cloning, A Laboratory Method,* Cold Spring Harbor Laboratory, Cold Spring Harbor, N.Y. (1982)]. Poly(A)RNA may be isolated by chromatography, such as on an olido-(dT) cellulose column and converted to cDNA using reverse transcriptase and double stranded using conventional technique [e.g., Land et al., 9 *Nucl. Acids Res.,* 2251 (1981)]. The DNA may be inserted into an available transformation vector and used to transform suitable cloning hosts such as *E. coli* K12. Digested plasmids obtained from the hosts are used to prepare a cDNA library and screened with a synthetic, labeled probe according to standard procedures [c.f. Southern, 98 *J. Mol Biol.* 503 (1975)]. Strongly hybridizing fragments may be used to construct an expression vector. Cells transformed with the expression vector may be used as a highly-producing source of PHF.

Using purified PHF, either from plasma, cultured producing cells or transformed cells, polyclonal and monoclonal antibodies and may be raised against PHF and used in any assay for PHF.

Male Balb/C mice were immunized by implantation of amino phenolthiol ether discs to which partially purified PHF from thyroparathyroid gland culture had been affixed, according to the procedure of Viamontes et al., *J. Immunol. Meth*, 94, 13–17 (1986). The mice were boosted with antigen in Freund's incomplete adjuvant at two-week intervals and the anti-body titre assayed by enzyme-linked immunosorbent assay (ELISA) using PHF isolated from plasma as the antigen. Detectable amounts of polyclonal antibodies were observed within one month and the titer increased thereafter.

Monoclonal antibodies may be prepared from the spleens of polyclonal antibody producing mice.

The required hybridoma and MCA may be obtained using the method of Langone and Van Vunakis, "Methods in Enzymology", 121, 1–947 (1986), using such modifications as are known to skilled practitioners in this art.

The method of detection using polyclonal and/or monoclonal antibodies is not specifically limited and includes radioimmunoassays, enzyme immunoassays, enzyme-linked immunosorbent assays, and assay systems based on the formation of an immunoprecipitate. A particularly desireable embodiment of such an assay system would be in the form of a diagnostic kit which could be used in a physician's office or a clinic, in the absence of sophisticated analytical instruments. Such methodology has been used for the detection of hormones and other immunoreactive substances in body fluids. One example is a commercially available kit for the detection of early pregnancy. PHF could, therefore, be qualitatively or quantitatively detected by the use of such methods.

A representative test kit for enzyme immunoassay would include a) an antibody to parathyroid hypertensive factor preferably bound to a solid phase; b) a secondary antibody labeled with an enzyme; c) a substrate for said enzyme label on said secondary antibody; and d) standard solutions of parathyroid hypertensive factor antibody factor. A representative test kit for RIA would include a) an antibody to parathyroid hypertensive factor; b) a secondary antibody to anti-parathyroid hypertensive factor; c) a standard solution of radiolabeled parathyroid hypertensive factor; d) a standard solution of unlabeled parathyroid hypertensive factor; and e) a precipitating reagent. A representative test kit for an immunoprecipitation assay would include a) an antibody to parathyroid hypertensive factor; b) a solid phase upon which said antibody attaches; and c) a standard solution of parathyroid hypertensive factor.

The identification of PHF provides an explanation of the seemingly anomalous reports in the literature that dietary calcium is often effective in lowering blood pressure and that calcium channel blockers are also effective in the same patient. One would expect that higher serum calcium ions would, over time, result in a higher intracellular calcium level and higher blood pressure. While not being specifically bound by a particular theory at this time, it appears that PHF operates to open calcium channels, as shown in FIG. 2, but that high levels of dietary calcium inhibit the release of PHF. Indeed, in SHR rats, we have shown that a calcium deficient diet caused an increase in plasma PHF which was absent in plasma of SHR rats fed a high calcium diet (Lewanczuk and Pang, Abstract, 4th Annual Meeting of the American Society of Hypertension, 1989).

This hypothesis is supported by infusion studies using other vaso active substances. When SD rats are infused with dialyzed SHR plasma and norepinephrine, arginine vasopressin (AVO) or angiotensin II (A-II), the increase in mean arterial pressure (MAP) was potentiated and the maximum increase was observed during peak hypertensive response to SHR plasma.

The presence of PHF appears to be characteristic of low renin and salt-sensitive forms of hypertension, but not of high renin or salt-insensitive forms.

The cellular origin of PHF in the parathyroid has been confirmed by parathyroidectomy of SHR rats, which resulted in a decrease in MAP. In addition, an unique cell type has been observed in the parathyroid glands of SHR, but not SD or WKY rats. The novel cells are observable by both light and electron microscopy. The cells have a dense and irregularly shaped nucleus with more intense staining of the cytoplasma using either aldehyde fuchsin or iron haematoxylin.

The availability of a PHF detection method allows the physician to perform a diagnostic test to identify the particular cause for essential hypertension and to select and monitor the appropriate therapy.

It has been found that the production of PHF(s), as well as renin, can be inhibited by supplemental calcium and that increased levels of supplemental calcium are effective in reducing hypertension. The effects of calcium supplementation are unpredictable due to the fact that high levels of calcium in the blood may increase the bio-availability of calcium to vascular smooth muscle tissue, limiting the anti-hypertensive effect. In addition, very high levels of dietary calcium may result in undesirable and painful calcium deposits in joints and may lead to kidney stones.

Any calcium supplement may be used which results in increased serum calcium levels. Calcium carbonate of mineral or oyster shell origin is preferred. Pharmaceutically acceptable examples are represented by Os-Cal ® (Marion) and Biocal ® (Miles).

The use of combination therapy involving both calcium, calcium channel blockers and dietary calcium supplementation allows the requisite lowering of blood pressure using smaller doses of the channel blocker while obtaining a greater anti-hypertensive effect. By "calcium channel blockers" is meant any pharmaceutical composition which inhibits the entry of calcium cells or inhibits the mobilization of calcium from intracellular cells. See, for example, Gilman et al., *The Pharmacological Basis of Experimental Therapeutics*, 7th ed., MacMillan, New York, 1985, pages 816–821. Representative examples of calcium channel blockers are dihydropyridines such as nifedipine, benzeneacetonitriles such as verapamil, and benzothiazepines such as diltiazem. As a result, not only is the therapy improved and side effects reduced, but the cost of treatment may be dramatically lowered, because the cost of calcium supplementation is much lower than the cost of available calcium channel blockers.

An effective alternative to the administration of calcium supplements, particularly when the diet contains adequate calcium, is to administer an effective form of Vitamin D, such as $1\alpha,25$-$(OH)_2D_3$, to increase calcium uptake in the duodenal mucosa. When calcium and/or $1\alpha,25$-$(OH)_2D_3$ is administered in combination with a calcium channel-blocker, it is preferable that the active components be combined in a single capsule containing appropriate unit doses of each. Patient compliance is improved when only one "medicine" is required.

The use of combination therapy involving a calcium channel blocker and calcium and/or an effective form of Vitamin D such as $1\alpha,25$-$(OH)_2D_3$ reduces the daily dosage of channel blocker required to less than half the dosage usually required, sometimes to as little as one-fifth of the dosage required for the channel blocker alone. The combination is compatible with other pharmaceutical compounds used for control of hypertension and angina such as angiotensin converting enzyme (ACE) inhibitors, $\beta$-adrenergic antagonists, nitrates, and diuretics.

A particular advantage of the combination of a calcium channel blocker and either or both of calcium and $1\alpha,25\text{-(OH)}_2D_3$ is the predictability of the therapy. The dose-response curve for nifedipine is not predictable in an individual patient, and a considerable period of time may be necessary to ascertain the appropriate dosage. The effect of exogenous calcium supplementation is not predictable, depending on numerous factors including rate of uptake, rate of excretion, parathyroid hormone levels and PHF levels. Somewhat surprisingly, therefore, it has been found that the combination of a calcium channel blocker and calcium supplement is not only synergistic, but that the dose response is more predictable. The time period over which a patient must be titrated is shortened and the potential for side effects is reduced because the therapeutic index is effectively raised.

The dosage of a combination pharmaceutical preparation which is used depends upon the needs of the individual patient. Typical formulations would be in capsule form containing 1/5 to ½ of the conventional dosage of a calcium channel blocker, with 500 mg of calcium carbonate and/or ca. 10-25 USP units (0.05 $\mu$g) of $1\alpha,25\text{-(OH)}_2D_3$. For example, a conventional dosage of nifedipine is 10 or 20 mg, given 2 to 3 times per day. A dosage according to this invention would include 5-10 mg/dose. Comparable convention dosages of verapamil are 80-120 mg and of dilthiazem is 30-60 mg/dose.

In addition to identification of essential hypertension, the existence of PHF and assays for PHF are applicable to the study and treatment of other diseases which may or may not necessarily include hypertension as a primary symptom. For example, non-insulin dependent diabetics frequently are hypertensive. Conversely, hypertensives frequently show an impaired glucose tolerance. In both circumstances, increased intracellular free calcium has been observed. PHF has been detected in the plasma of Ob/Ob mice, which are obese, hypertensive and have non-insulin dependent diabetes. The PHF from these mice has been isolated in the sera in the same subfraction as PHF from SHR rats. Detection of PHF may be useful in diagnosis of non-insulin dependent diabetes (NIDDM) and may open a new area of research into the role of PHF in NIDDM.

Some forms of cancer are characterized by an increase in intracellular free calcium [see: Okazaki et al., Canc. Res., 46 (12 Pt 1), 6059-6063 (1986); Lipton and Morris, Canc. Chemother. Pharmacol., 18(1), 17-20 (1986); Chien and Warren, Canc. Res., 46(11), 5706-5714); Shirakawa et al., Canc. Res., 46(2), 658-661 (1986); and Meyer, J. Hypertens., 5 (suppl. 4), S3-S4 (1987)]. Parathyroid activation also has been associated with certain forms of cancer [see: Palmer et al., Am. J. Epidemiol., 127(5), 1031-1040 (1988) and Feig and Gottesman, Cancer, 60(3), 429-432 (1987)]. As PHF is of parathyroid origin, and as preliminary data suggests that PHF can increase intracellular calcium levels, PHF may be implicated in these and other forms of cancer. Thus, screening for PHF may be valuable in understanding the etiology of these cancers as well as in developing detection methods and therapeutic regimens.

The following examples illustrate this invention but are not limiting thereof. Various modifications may be apparent to those skilled in the art without deviating from the scope of this invention.

EXAMPLE 1

Demonstration of the Presence of PHF in SHR Rats

Male rats of the SHR, Wistar-Kyoto (WKY) and Sprague-Dawley (SD) strains were decapitated and exsanguinated and the pooled blood from each strain was heparinized (100 IU/ml) and centrifuged at $3K \times g$ for 10 min. at 4° C. The plasma obtained was dialyzed against distilled water using a membrane having a molecular weight cutoff of 1,000 daltons.

SD rats were anesthetized using Na pentobarbital, (50 mg/kg, i.p.) and catheters were inserted in the jugular vein for injection of plasma and drugs and in the carotid artery of measurement of b.p.

Plasma was administered either by infusion at a rate of 3 ml/kg/hr or in a series of boli, each bolus being 2.5 ml/kg.

FIG. 4 shows the change in mean arterial pressure over time for the infusion of plasma from SHR, WKY and SD rats into SD rats. After 105 min., the SHR plasma infusion was terminated and SD plasma substituted, resulting in a return to the baseline b.p. within 30 min.

Figure 5:
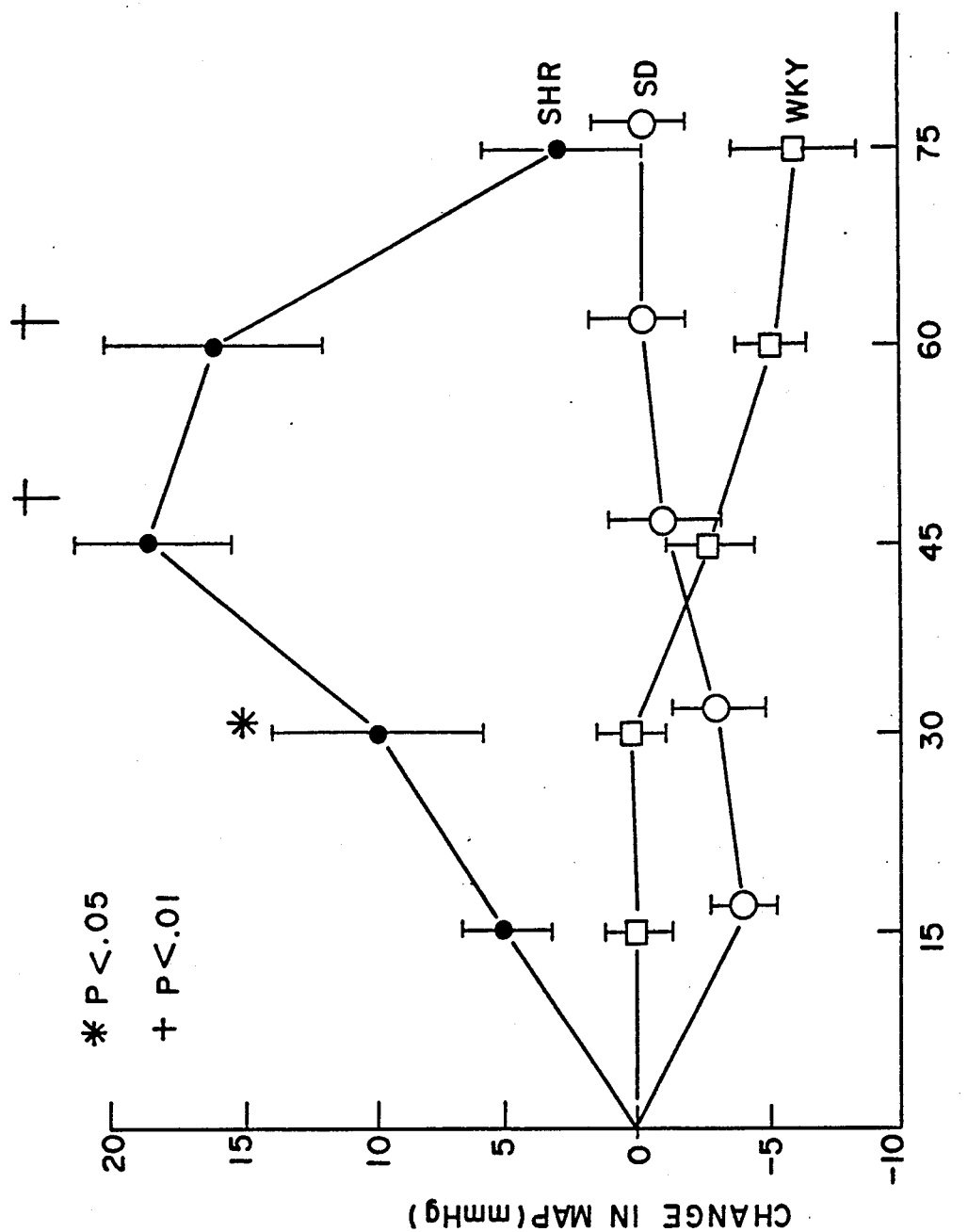
FIG. 5 shows the change in mean arterial pressure in SD rats administered boli of plasma obtained from SHR, SD and WKY rats.

The effect of bolus administration of SHR, WKY and SD plasma on SD rats is shown in FIG. 5. The time course of b.p. change, but not the relative effect is similar to FIG. 4.

EXAMPLE 2

Control of Calcium Uptake

Figure 6:
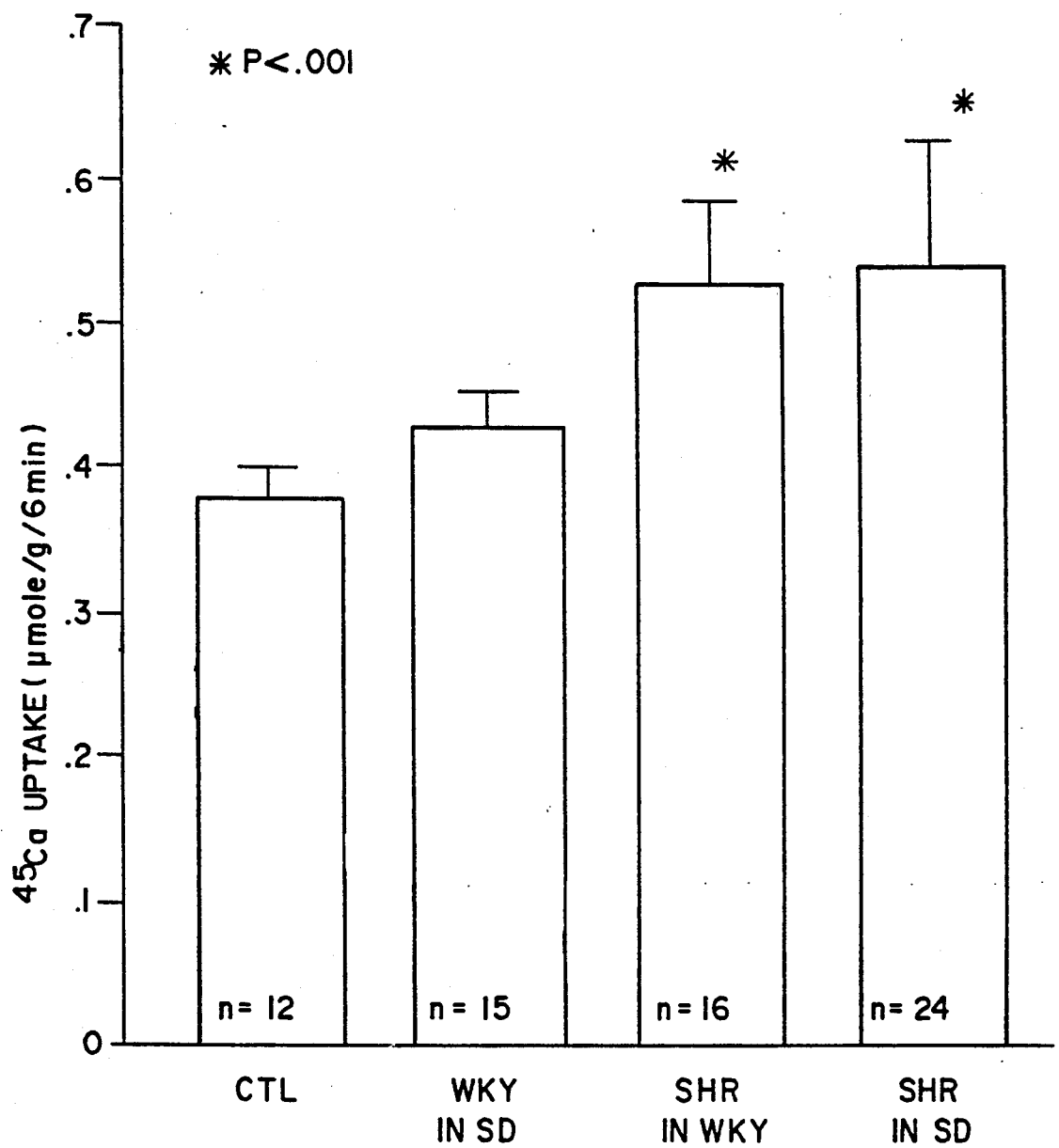
FIG. 6 shows the uptake of the $^{45}Ca$ in rat tail arterial sections incubated in Krebs buffer containing plasma from SD, WKY and SHR rats.

Calcium uptake [$^{45}$Ca] was measured in SD tail arteries in vitro using the low-affinity lanthanum-resistant pool method as described in Pang et al., Life Sci., 42, 1935 (1988). Rat tail artery strips were equilibrated in oxygenated (95% $O_2$, 5% $CO_2$) Krebs-Hanseleit buffer for 2 hours. After equilibration, the strips were incubated in 30% plasma in Kreb's buffer in the presence of 0.1 $\mu$ Ci $^{45}$Ca. After the predetermined incubation time, tissues were rinsed in cold, $Ca^{2+}$-free, $La^{3+}$ containing solution, blotted, weighed and digested as described in Pang et al., Life Sci., 42, 1935 (1988). Ca uptake was determined in a scintillation counter and is shown in FIG. 6. The uptake of $^{45}$Ca follows the curve for b.p. increase and is dose dependent.

EXAMPLE 3

Isolation of PHF by Exclusion Chromatography

Plasma from SHR, WKY and SD rats was dialyzed against distilled water overnight (1,000 mwco) and filtered using an Amicon ultra-filtration cell (5,000 mwco) chromatographed on a column packed with Bio-Gel P-6 eluting with 0.05 M ammonium acetate and the eluted fractions were measured at 280 nm using a Pharmacia U.V. photometer. Aliquots of 6.67 ml were collected. A fraction having a molecular weight of approximately 3,500 daltons was observed in the SHR plasma but not in the plasma from WKY or SD rats (FIG. 1). Molecular weight markers used to size the column were ACTH (m.w. 4541.7), insulin B chain (m.w. 3496), insulin A chain (m.w. 2530) and a 13 amino acid synthetic peptide (m.w. 1464).

Figure 7:
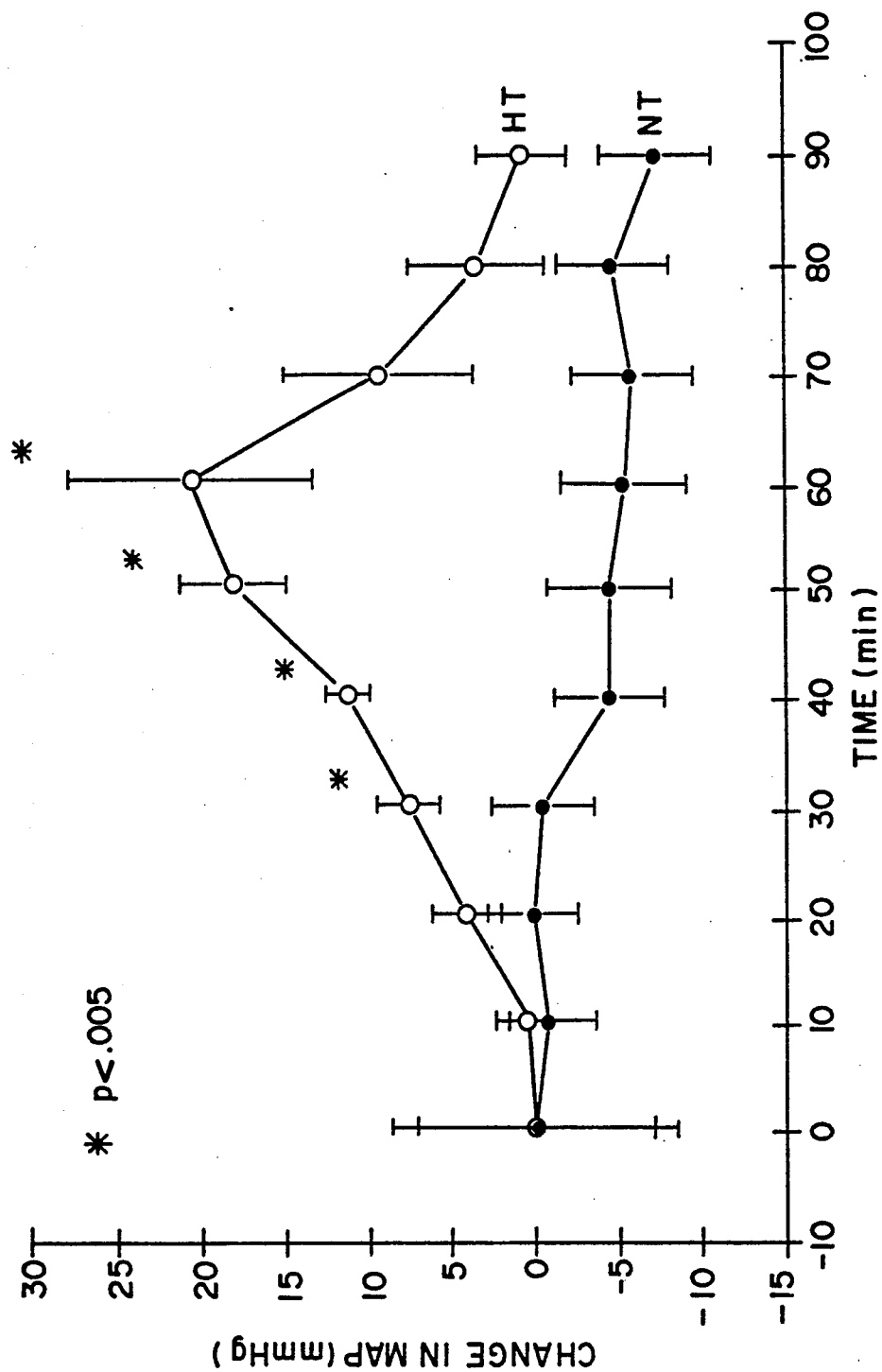
FIG. 7 shows the change in mean arterial pressure in SD rats administered the anomalous fraction of plasma isolated by molecular exclusion chromatography from SHR rats.

The unique fraction from SHR rats was concentrated by freeze drying and injected into a SD rats catheterized as described in Example 1. An increase in b.p. comparable in onset time and magnitude to plasma from SHR rats was observed. The data are shown in FIG. 7.

EXAMPLE 4

Purification of PHF by HPLC

The unique fraction obtained in Example 3 was lyophilized, and fractionated on a Brownlee RP-P (C-8) reverse phase column HPLC using a solvent gradient of 0.1% trifluoroacetic acid: acetonitrile, monitoring at 280 nm. The biological activity was found in a peak [See FIG. 2(a)] which did not appear in a plasma sample obtained form WKY rats FIG. 2(b)].

EXAMPLE 5

Isolation from Cell Culture

Thyroparathyroid glands were excised from SHR and WKY rats. The glands were cultured in Hank's medium, the media being changed daily Pooled media was dialyzed against distilled water and filtered using the same procedures used to treat blood plasma. The fraction, having a molecular weight between 1,000 and 5,000, was lyophilized and fractionated on a Brownlee RP-P (C-8) reverse phase column HPLC, using a gradient of 0.1% trifluoroacetic acid: acetonitrile, monitoring at 280 nm. An active fraction from SHR eluted in the same position as in plasma, and no corresponding fraction was found in the medium from WKY rat cells. FIG. 8(a) shows the elution profile of media from SHR cell lines; FIG. 8(b) shows the WKY rats.

EXAMPLE 6

Separation of Culture Media on SDS-PAGE

Mini SDS-PAGE slab gels containing 15–18% acrylamide/bisacrylamide (Bio-Rad) containing Tris (pH 8.8) in a Tris buffer (pH 8.3) were loaded with lyophilized and resuspended ($H_2O$) cell culture media from cultures of SHR and SD thyroid glands prepared as described in Example 5. The gels were run for about 1 hour at 200 V (Bio-Rad Mini-Protein II). The results are shown in FIGS. 10(a)–(d).

EXAMPLE 7

Separation of Cell Extracts on SDS-PAGE

Figure 9A:
FIG. 9(a) is an SDS-PAGE gel scan using a 14 KD standard.
Figure 9B:
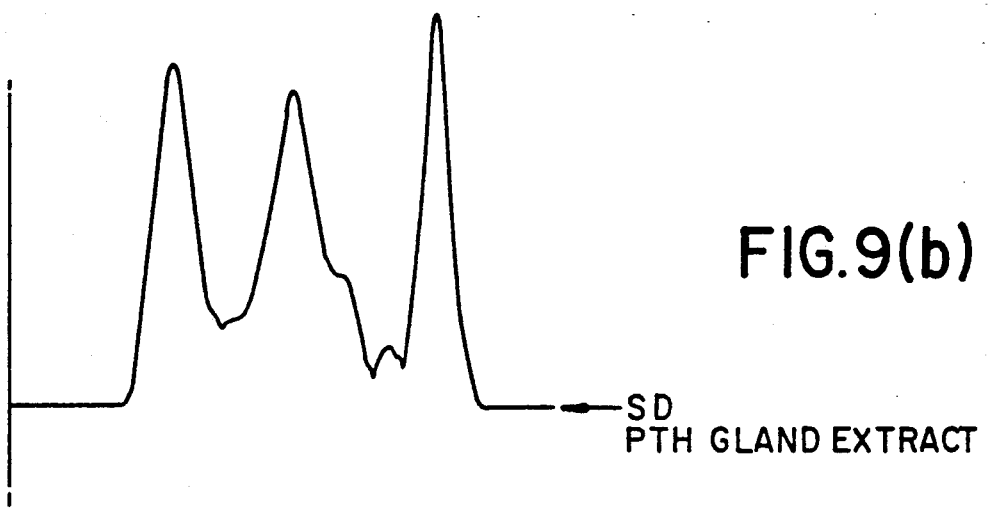
FIG. 9(b) is a gel scan for a gland extract from the thyroparathyroid of an SD rat after 8 hours incubation.
Figure 9C:
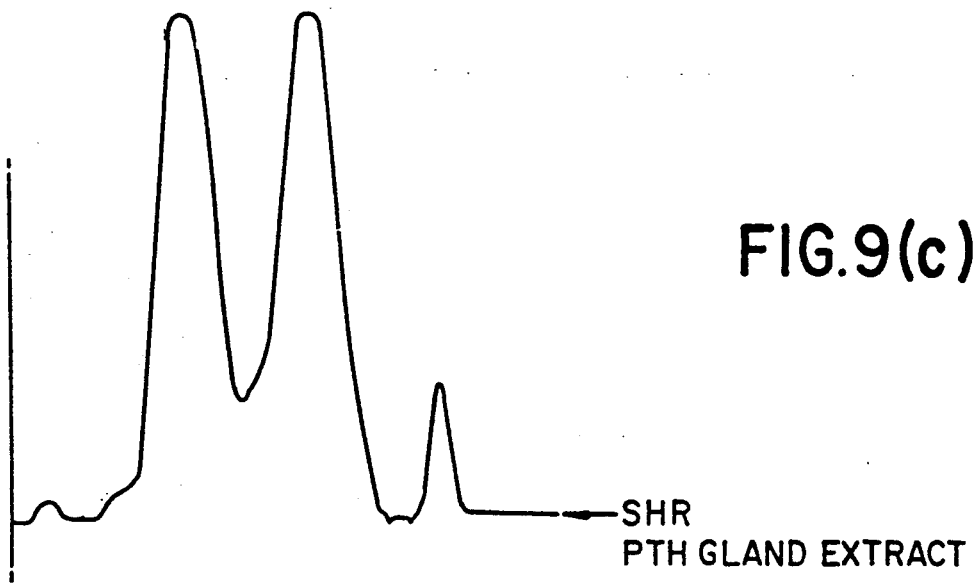
FIG. 9(c) is a gel scan of a gland extract from the thyroparathyroid of an SHR rat after 8 hours incubation.
Figure 10A:
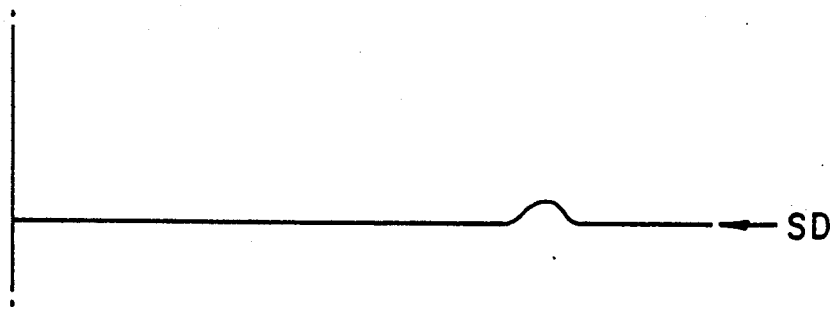
FIG. 10(a) is a scan of an SDS-PAGE gel run on culture media from Sprague-Dawley thyroid cells (12 hour culture).
Figure 10B:
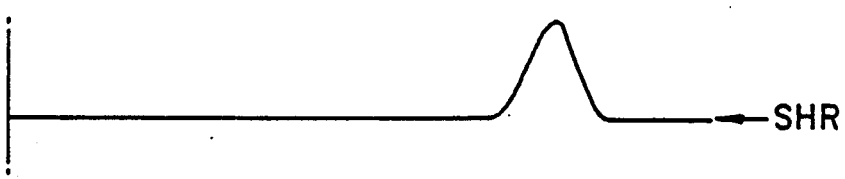
FIG. 10(b) is a comparative scan using thyroid from SHR rats after 4 hours culture.
Figure 10C:
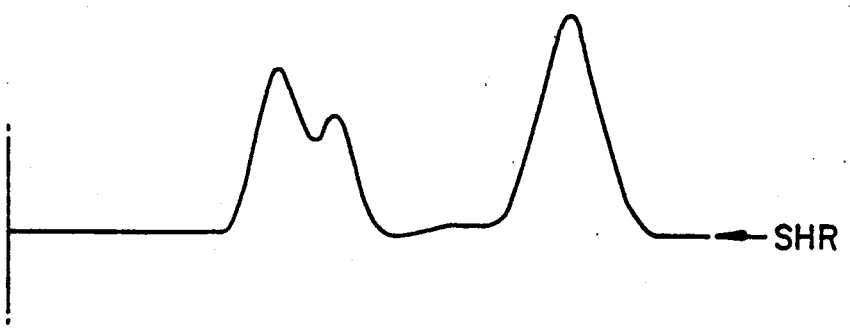
FIG. 10(c) is a scan of culture media from SHR thyroid culture after 12 hours culture.
Figure 10D:
FIG. 10(d) is gel scan using a 14 KD standard.

Thyroparathyroid cells from SHR and SD rats, cultured in Hank's media for 8 hours were isolated and homogenized in 50 mM acetic acid, centrifuged at 5,000×g and loaded on a 10–18% acrylamide/bisacrylamide slab gel and developed for 1 hour at 200 V. The results are shown in FIGS. 9(a)–(c).

EXAMPLE 8

Isoelectric Focusing

Analytical isoelectric focusing of column fractions were performed using a Bio-Rad Model 111 Mini-IEF cell. This technique separates proteins on the basis of isoelectric point, and the results indicate the purity of the column fraction isolated according to Example 3. The procedure used is that described by Righetti in "Isoelectric Focusing Theory, Methodology and Applications", Elsevier Biomedical Press, Amsterdam (1983), as modified by Bio-Rad Model 111 Mini IEF Cell Instruction Manual, Bio-Rad Labs., Richmond, Calif. A thin slab of polyacrylamide gel, containing ampholytes, (pH 3–10) is cast on a gel support film. Samples purified from SHR plasma and thyroparathyroid cell cultures, together with standards, were applied to the gel, and then the gel put directly onto graphite electrodes Proteins were focussed over the course of 60–90 min. Protein bands were stained with a stain containing both Coomassie blue and Crocein scarlet. The results are shown in FIG. 17. A band at ca. pH 6 appears in both plasma and culture media.

EXAMPLE 9

Production of Polyclonal Antibodies

Male Balb/C mice have been immunized with a partially pure preparation of PHF (20–30% purity). The amount of PHF in the preparation has been estimated on the basis of the 210 nm absorbance. Peptide samples, each containing approximately 10 µg of PHF, were coupled to aminophenyl thioether-derivatized (APT) paper discs by diazo linkages, according to the procedure described by Viamontes et al. (J. Immun. Metho. 94, 13–17, 1986). An aliquot of 0.3 ml of a 10 mg/ml solution of $NaNO_3$ in doubly-distilled water was added to 10 ml aliquots of 1.2 N HCl. A 0.3 ml aliquot of the $NaNO_3$/HCl solution was added to the top of each of 6 mm APT discs and the discs were set in a dish and held at 4° C. for 30 minutes on a shaker. The discs were washed with cold distilled water, 0.2 M NaOAc buffer (pH 4) and dried. The derivatized paper discs were then soaked in Freund's complete adjuvant, and implanted i.p. In two weeks the titer of anti-PHF was determined by ELISA, and the mice reinoculated (boosted) as described above, except that the disc was implanted with Freund's incomplete adjuvant. The titer was checked 1 week later by ELISA. The mice were boosted at two week intervals and samples assayed by the following ELISA method.

Figure 11:
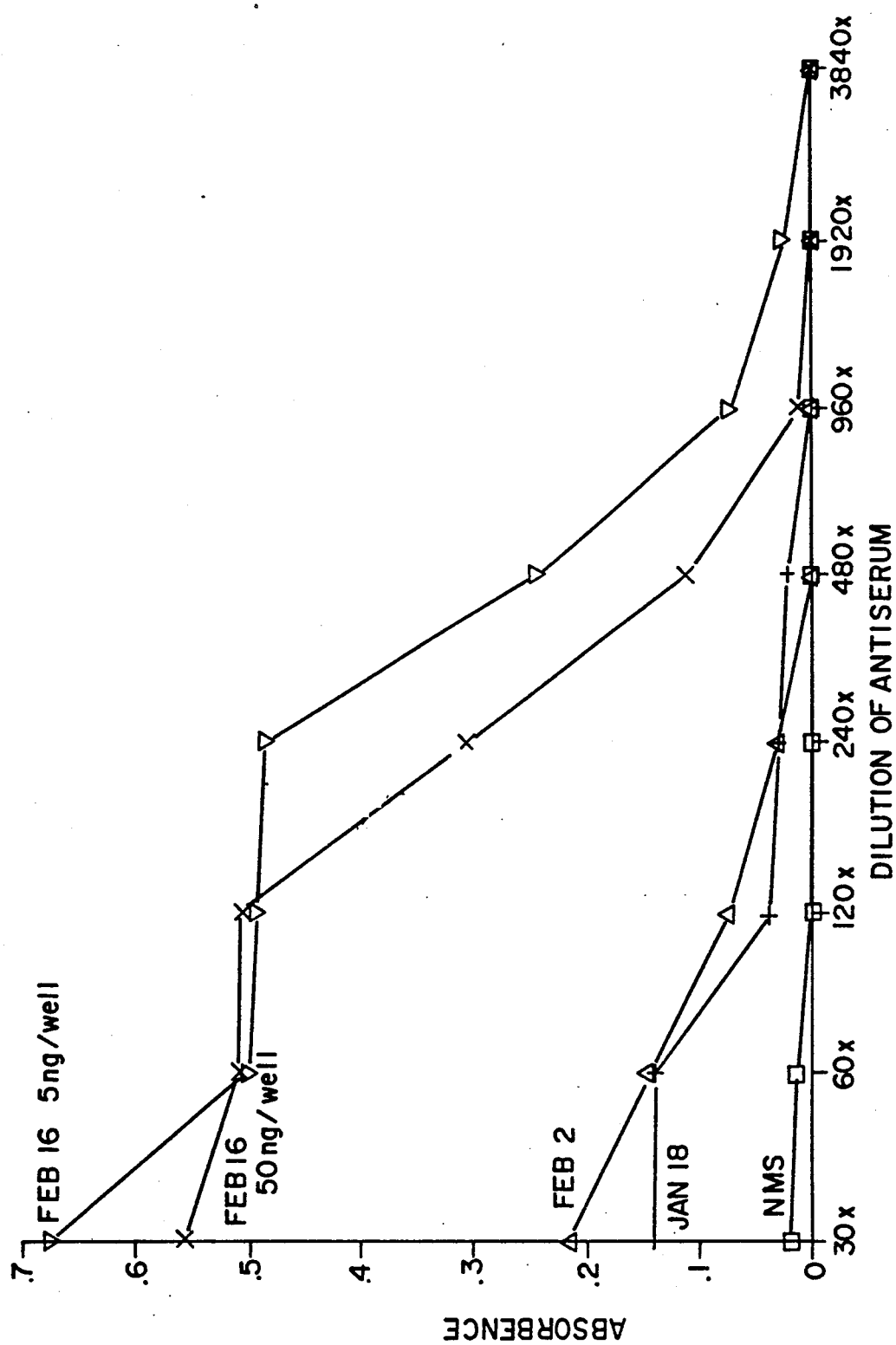
FIGS. 11 and 12 are graphical representations of the data shown in Table 1.
Figure 12:
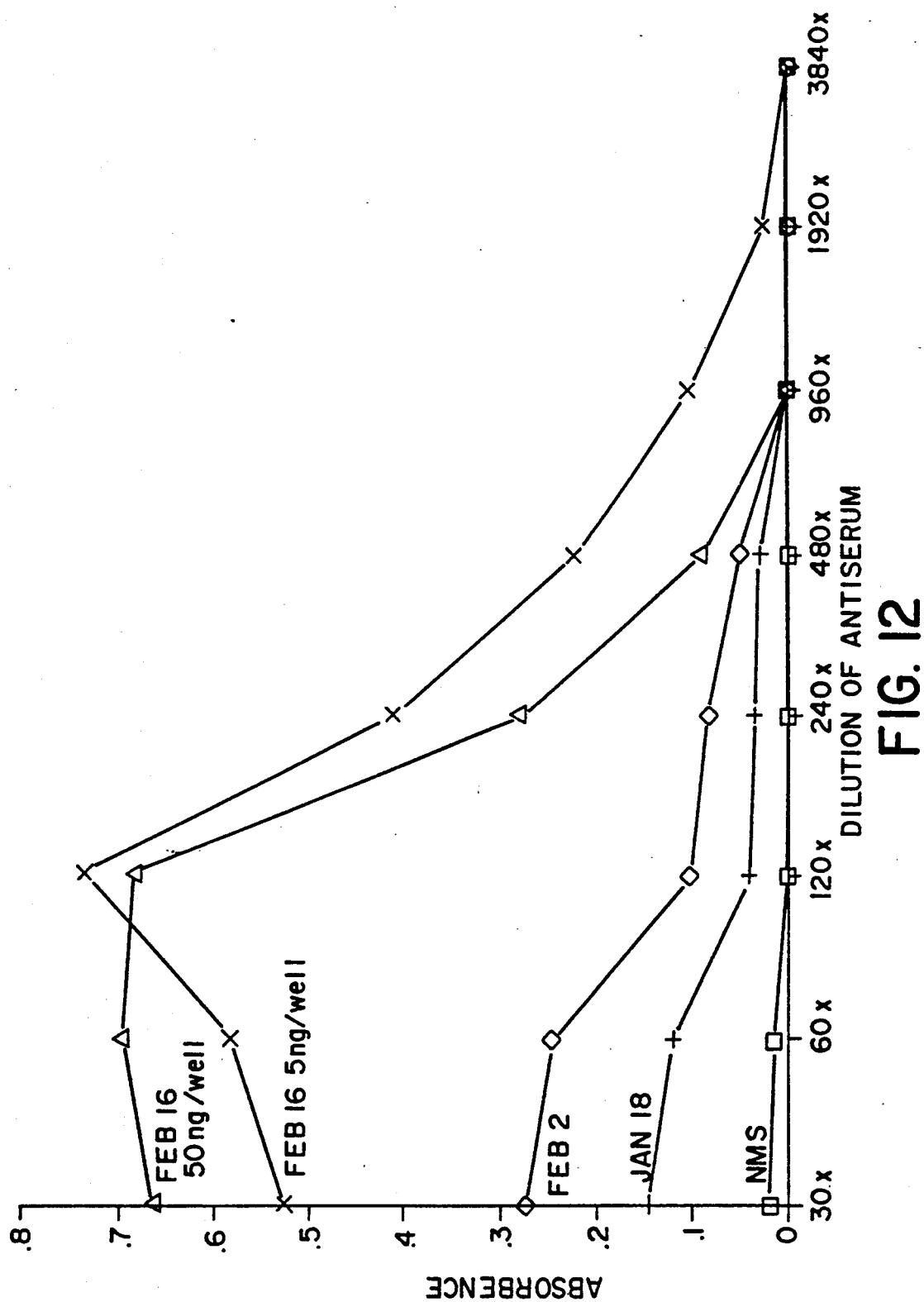

Plates were coated with 100 µl/well of 500 ng/ml PHF in Tris buffer (pH 9.0), stored overnight and washed with phosphate buffered saline-Tween 20, then three times with PBS. The plates were then coated with 0.2% gelatin in PBS, incubated 30 minutes at 37° C., and washed with PBS-Tween 20 three times. Immunized serum, obtained from the mice described above, was added (100µl/well in 1% gelatin PBS-Tween 20 at dilutions of (results and procedure conflict) and the plates incubated for 1 hour at room temperature, then washed with PBS-Tween 20 three times. Horse radish peroxidase (1:2000) in 1% gelatin PBS-Tween 20 was added in an amount of 100 µl/well, incubated for 1 hour at room temperature and the plates were washed with PBS-Tween 20. A freshly prepared solution of 10 ml citric acid, 0.05 M pH 4, 100 µl 2,2′-azinobis(3-ethyl-benzthiazoline sulfonic acid), 20 mg/ml and 40 of hydrogen peroxide solution was added in an amount of 100 µl/well and read at 405 nm after incubation for 1 hour at room temperature (Titer-Tek Multi Scan). The results are shown in Table 1 and plotted in FIGS. 11 and 12.

EXAMPLE 10

Feeding of Combinations of Agents

Male rats of the SHR strain, obtained from Harlan Sprague-Dawley, 12 weeks old, were divided into groups of 12 or 24, and were fed prepared diets containing 0.2%, 0.4% and 0.8% elemental calcium, respectively. Also included in the diet were 0, 50, 150 and 300 mg/kg of food of nifedipine. Distilled water was available ad lib. Feeding was continued for 8 weeks and the mean blood pressure of each animal was determined at the end of that time. The data are shown in Table 2.

From the Table, it can be seen that SHR rats on a normal diet, (0.2% dietary calcium) and which did not receive nifedipine, showed an average blood pressure of 176 mm Hg. The highest does of nifedipine, 300 mm/kg, resulted in a decrease in blood pressure of approximately 10 mm Hg. Using 4 times the amount of ordinary dietary calcium, the decrease in blood pressure was shown to be measurable, but small. When maximum dietary calcium and nifedipine were coadministered, blood pressure could be reduced to approximately 120 mm Hg, or a decrease of approximately 56 mm Hg, or 32% (the level found in normotensive rats).

Nifedipine in amounts of 50 or 150 mg/kg of food decreased mean blood pressure by 20 mm Hg, but supplementation with 0.8% calcium reduced mean blood pressure by approximately 40 to 60 mm Hg. A combination of nifedipine and dietary supplemental calcium produced a predictable and nearly linear dose response with increased efficacy when compared to either agent alone. The data is suggestive of a synergistic relationship between the two agents.

EXAMPLE 11

Formulation I

A capsule containing a calcium channel blocker and a calcium supplement may be prepared using conventional techniques according to the following formulation:

| Nifedipine | 5 mg. |
|---|---|
| CaCO$_3$ | 500 mg. |
| gelatin (soft) | 1,495 mg. |

EXAMPLE 12

Formulation II

A capsule containing a calcium channel blocker and 1α,25-(OH)$_2$D$_3$ may be prepared using conventional techniques according to the following formulation:

| Nifedipine | 5 mg. |
|---|---|
| 1α,25-(OH)$_2$D$_3$ | 0.05 μg. |
| gelatin (soft) | 1,745 mg. |

TABLE 1

| Dilution Control | NMS** * | 4 weeks * | 6 weeks * | 8 weeks * | 8 weeks (5 ng/well) |
|---|---|---|---|---|---|
| Mouse #1 | | | | | |
| 30 | 0.019 | 0.141 | 0.216 | 0.557 | 0.674 |
| 60 | 0.013 | 0.138 | 0.145 | 0.509 | 0.499 |
| 120 | 0 | 0.038 | 0.075 | 0.506 | 0.492 |
| 240 | 0 | 0.031 | 0.030 | 0.306 | 0.483 |
| 480 | 0 | 0.021 | 0 | 0.111 | 0.242 |
| 960 | 0 | 0 | 0 | 0.012 | 0.071 |
| 1920 | 0 | 0 | 0 | 0 | 0.024 |
| 3840 | 0 | 0 | 0 | 0 | 0 |
| Mouse #2 | | | | | |
| 30 | 0.019 | 0.144 | 0.272 | 0.662 | 0.526 |
| 60 | 0.013 | 0.118 | 0.243 | 0.692 | 0.581 |
| 120 | 0 | 0.041 | 0.103 | 0.681 | 0.733 |
| 240 | 0 | 0.035 | 0.085 | 0.279 | 0.410 |
| 480 | 0 | 0.031 | 0.051 | 0.091 | 0.222 |

TABLE 1-continued

| Dilution Control | NMS** * | 4 weeks * | 6 weeks * | 8 weeks * | 8 weeks (5 ng/well) |
|---|---|---|---|---|---|
| 960 | 0 | 0 | 0 | 0 | 0.104 |
| 1920 | 0 | 0 | 0 | 0 | 0.026 |
| 3840 | 0 | 0 | 0 | 0 | 0 |

Note:
* 50 ng/well
**Normal Mouse Serum

TABLE 2

Synergistic Effect of Calcium and Nifedipine on Blood Pressure in SHR

| Nifedipine (mg/kg food) | Dietary Calcium (% as elemental Ca) | | |
|---|---|---|---|
| | 0.2% | 0.4% | 0.8% |
| 0 | 176 ± 5 | 164 ± 6 | 169 ± 6 |
| 50 | 145 ± 7 | 154 ± 5 | 133 ± 7 |
| 150 | 147 ± 8 | 136 ± 4 | 119 ± 9 |
| 300 | 167 ± 7 | 125 ± 7 | 118 ± 5 | p = .0034 for interaction
p < .0001 for calcium effect
p < .000 for nifediprine effect

We claim:

1. Substantially pure parathyroid hypertensive factor.

2. Substantially pure parathyroid hypertensive factor according to claim 1 having a molecular weight of about approximately 3,000 to 4,000 daltons.

3. The substantially pure parathyroid hypertensive factor according to claim 2 having the property of delayed onset of an increase in blood pressure of a normotensive rat when administered thereto, said increase in blood pressure temporally correlating with an increase in extracellular calcium uptake by vascular smooth muscle.

4. A method for the preparation of substantially pure parathyroid hypertensive factor comprising:
  (a) isolating blood plasma from a hypertensive mammal;
  (b) removing components having a molecular weight less than 1,000 daltons from said plasma by dialysis against distilled water to obtain a dialysate;
  (c) separating plasma components having a molecular weight lower than 5000 daltons from said dialysate by ultrafiltration to obtain a filtrate;
  (d) concentrating the filtrate by lyophilization to obtain a concentrate;
  (e) fractionating said concentrate on a molecular sieve column and eluting to obtain a plurality of fractions and identifying the fraction having hypertensive factor activity;
  (f) concentrating said fraction having parathyroid hypertensive factor activity by lyophilization; and
  (g) purifying the fraction obtained in step (f) by reverse phase HPLC.

5. A method for detecting the presence of parathyroid hypertensive factor comprising:
  (a) raising polyclonal antibodies in a vertebrate by injecting a solution containing mammalian parathyroid hypertensive factor into said vertebrate;
  (b) collecting serum containing polyclonal antibodies raised against parathyroid hypertensive factor;
  (c) screening a sample which may contain parathyroid hypertensive factor by an immunoassay method using said polyclonal antibodies; and
  (d) detecting the presence of parathyroid hypertensive factor in said sample.

6. The method according to claim 5, wherein the immunoassay method is an enzyme linked immunoassay.

7. The method according to claim 5, wherein the immunoassay method is an enzyme linked immunosorbent assay.

8. The method according to claim 5, wherein the immunoassay method is an immunoprecipitation assay.

9. A method for the identification of parathyroid hypertensive factor in a patient comprising:
   (a) raising antibodies to parathyroid hypertensive factor by injecting parathyroid hypertensive factor into a vertebrate;
   (b) isolating antibody-secreting B-lymphocytes from said immunized vertebrate;
   (c) fusing said antibody-secreting B-lymphocytes with myeloma cells to form hybridomas;
   (d) selecting and cloning said hybridomas which secrete parathyroid hypertensive factor antibody;
   (e) propagating said antibody-secreting hybridomas;
   (f) isolating a monoclonal antibody from said hybridomas; and
   (g) screening a sample from a mammal which may contain parathyroid hypertensive factor by an immunoassay method using said monoclonal antibodies.

10. The method according to claim 9, wherein the immunoassay method is an enzyme linked immunoassay.

11. The method according to claim 9, wherein the immunoassay method is an enzyme linked immunosorbent assay.

12. The method according to claim 9, wherein the immunoassay method is an immunoprecipitation assay.

13. A method for the identification of a cause of essential hypertension in a mammal comprising testing said mammal for the presence of parathyroid hypertensive factor.

14. A kit for the detection of parathyroid hypertensive factor in a mammal, comprising, in a single package:
   a) an antibody to parathyroid hypertensive factor bound to a solid phase;
   b) a secondary antibody to anti-parathyroid hypertensive factor antibody labeled with an enzyme;
   c) a substrate for said enzyme label on said secondary antibody; and
   d) standard solutions of parathyroid hypertensive factor.

15. A kit for the detection of parathyroid hypertensive factor in a mammal, comprising, in a single package:
   a) an antibody to parathyroid hypertensive factor;
   b) a solid phase upon which said antibody attaches; and
   c) a standard solution of parathyroid hypertensive factor.

* * * * *